(12) United States Patent
Kittle et al.

(10) Patent No.: US 7,659,316 B2
(45) Date of Patent: Feb. 9, 2010

(54) FOAM COMPOSITION

(75) Inventors: Paul A. Kittle, Concordville, PA (US); David C. Dehm, Thornton, PA (US)

(73) Assignee: Rusmar Incorporated, West Chester, PA (US)

( * ) Notice: Subject to any disclaimer, the term of this patent is extended or adjusted under 35 U.S.C. 154(b) by 177 days.

(21) Appl. No.: 11/787,049

(22) Filed: Apr. 13, 2007

(65) Prior Publication Data

US 2008/0255255 A1   Oct. 16, 2008

(51) Int. Cl.
*B01D 17/05* (2006.01)

(52) U.S. Cl. ......................................... 516/140; 252/60

(58) Field of Classification Search ................... 516/140
See application file for complete search history.

(56) References Cited

U.S. PATENT DOCUMENTS

| | | | |
|---|---|---|---|
| 1,985,491 A | 12/1934 | Fisher | |
| 2,875,555 A | 3/1959 | Thiegs | |
| 3,466,873 A | 9/1969 | Present | |
| 3,563,461 A | 2/1971 | Cole | |
| 3,669,898 A | 6/1972 | Butler | |
| 3,891,571 A | 6/1975 | Lambou | |
| 4,086,331 A | 4/1978 | Neumann | |
| 4,127,383 A | 11/1978 | Johnston | |
| 4,421,788 A | 12/1983 | Kramer | |
| 4,474,680 A | 10/1984 | Kroll | |
| 4,519,338 A | 5/1985 | Kramer | |
| 4,795,590 A | 1/1989 | Kent | |
| 4,874,641 A | 10/1989 | Kittle | |
| 4,923,903 A | 5/1990 | Alm | |
| 5,026,735 A | 6/1991 | Stern | |
| 5,096,616 A | 3/1992 | Kittle | |
| 5,215,786 A | 6/1993 | Kittle | |
| 5,225,095 A * | 7/1993 | DiMaio et al. | ................. 516/14 |
| 5,434,192 A | 7/1995 | Thach | |
| 5,556,033 A | 9/1996 | Nachtman | |
| 5,696,174 A | 12/1997 | Chao et al. | |
| 5,849,364 A | 12/1998 | Nachtman | |
| 5,853,050 A | 12/1998 | Kittle | |
| 5,897,946 A | 4/1999 | Nachtman | |
| 6,096,373 A | 8/2000 | Nachtman | |
| 6,833,359 B1 * | 12/2004 | Lazarovits | ................... 514/22 |
| 6,929,423 B2 | 8/2005 | Kittle | |
| 6,994,491 B2 | 2/2006 | Kittle | |
| 7,022,651 B1 | 4/2006 | Lightcap | |

OTHER PUBLICATIONS

Lim et al., "Cationic Oat Starch: Preparation and Effect on Paper Strength", Cereal Chemistry, vol. 69, No. 3, 1992, p. 237-239.*
Hofreiter, B.T., "Natural Products for Wet-End Addition," in "Pulp and Paper Chemistry and Chemical Technology," Casey, J.R., editor, Wiley, New York, NY, 3rd Edition, 1981, pp. 1475-1514.
Paschall, E.F., "Production and Uses of Cationic Starches," in "Starch Chemistry and Technology," Whistler, R.L. and Paschall, E.F., editors, Academic Press, New York NY, vol. II, pp. 403-422, 1984.
Perri, J.M., "Fire Fighting Foams", in Bikerman, J.J., "Foams: Theory and Industrial Applications," Reinhold Publishing Corporation, New York, NY, 1953. pp. 189-243.
Smith, R.J., "Characterization and Analysis of Starches," in "Starch Chemistry and Technology," Whistler, R.L. and Paschall, E.F., editors, Academic Press, New York, NY, vol. II, pp. 569-635, 1984.
Whistler, R.L., Bemiller, J.N., and Paschall, E.F., "Starch: Chemistry and Technology," Second Edition, Academic Press, New York, NY, 1984. pp. 264-265; pp. 312-315; pp. 354-363; p. 612.
"Nitrogen in Starch, Starch Slurry, and Glucose," Organic Application Note, LECO Corporation, 3000 Lakeview Avenue, St. Joseph, MI 49085; 2003.

* cited by examiner

*Primary Examiner*—Ling-Siu Choi
*Assistant Examiner*—Chun-Cheng Wang
(74) *Attorney, Agent, or Firm*—Howson & Howson LLP

(57) ABSTRACT

Foams suitable for such uses as landfill coverage, frost protection, volatile emission control, gas control in mining, are composed of a hydrolyzable protein and a pre-gelatinized cationic modified starch along with other ingredients. The foam concentrate can be made at ambient temperature, is stable over time, can be easily tailored to achieve a desired foam stiffness and drain time characteristic over wide ranges, and can be easily diluted at ambient temperature to produce a foamable composition.

20 Claims, 2 Drawing Sheets

FOAM COMPOSITION

FIELD OF THE INVENTION

This invention relates generally to water-based (aqueous) foam compositions, and more particularly to protein foam concentrates containing ingredients which can be altered easily in order to change the characteristics of the resulting foam dramatically.

BACKGROUND OF THE INVENTION

The most common industrial aqueous foam applications use the produced foam as a barrier, often between a substrate and the surrounding atmosphere. The most widely known barrier application is fire fighting where a foam barrier separates a burning substrate from oxygen. This application is described in Perri, J. M., "Fire Fighting Foams", in Bikerman, J. J., "Foams: Theory and Industrial Applications," Reinhold Publishing Corporation, New York, N.Y., 1953. Although, in the case of a fire fighting foam, the heat generated by the fire destroys the applied foam, extinguishment occurs because the foam application overwhelms the burning substrate.

There are many other barrier foams which are not related to fire extinguishing. For example, various barrier foams are described in United States patents. Alm U.S. Pat. No. 4,923,903, Chao U.S. Pat. No. 5,696,174, DiMaio U.S. Pat. No. 5,225,095, Fisher U.S. Pat. No. 1,985,491, Johnston U.S. Pat. No. 4,127,383, Kent U.S. Pat. No. 4,795,590, Kittle U.S. Pat. Nos. 4,874,641, 5,096,616, 5,215,786 and 5,853,050, Kramer U.S. Pat. Nos. 4,421,788 and 4,519,338, Nachtman U.S. Pat. Nos. 5,556,033, 5,849,364, 5,897,946 and 6,096,373, Present U.S. Pat. No. 3,466,873, Stern U.S. Pat. No. 5,026,735, Thach U.S. Pat. No. 5,434,192, describe the use of foams for landfill coverage or volatile emissions applications. Butler U.S. Pat. No. 3,669,898, Cole U.S. Pat. No. 3,563,461, Lambou U.S. Pat. No. 3,891,571, Lightcap U.S. Pat. No. 7,022,651, Neumann U.S. Pat. No. 4,086,331, and Thiegs U.S. Pat. No. 2,875,555 describe the use of foams for frost protection. In these examples, foam barriers separate a solid or liquid substrate from the atmosphere, thereby inhibiting mass or heat transfer.

With the exception of fire fighting foams, which are partially consumed during application, in general, barrier foams need to exhibit persistence after they have been applied. In each of the application areas mentioned above, landfills, volatile emissions, and frost protection, the applied foam should remain essentially unchanged for a relatively long time interval, e.g., 10-12 hours, or overnight, in order to minimize application costs. To satisfy this performance parameter, the "drain time," which is usually expressed in terms of rate of drainage (% of sample per minute, rather that in terms of time), needs to be reduced, i.e., the drainage is slowed down, so that the amount of decomposition is only a small percentage of the total volume of the initially applied foam in the desired 10-12 hour interval. The general chemical approach used to reduce the drain time involves increasing the surface viscosity of the foam bubbles, in theory, but in practice, this is reduced to increasing the viscosity of the foamed material, most desirably, after the foaming operation has been completed.

There are three general methods to achieve this final viscosity result: (a) use a composition which crosslinks after foaming, as in the following United States patents: Alm U.S. Pat. No. 4,923,903, Chao U.S. Pat. No. 5,696,174, Kent U.S. Pat. No. 4,795,590, Kramer U.S. Pat. Nos. 4,421,788 and 4,519,338, Stern, or (2) use a composition which gels after foaming as in the following United States patents: DiMaio U.S. Pat. No. 5,225,095, Kittle U.S. Pat. No. 5,853,050, and Neumann U.S. Pat. No. 4,086,331, or (3) use a composition which provides a somewhat rigid and insoluble system after foaming, such as stearate salts, as in the following United States patents: Kittle U.S. Pat. Nos. 4,874,641, 5,096,616 and 5,215,786. It is notable that both the starch/gum systems and the stearate systems are similar in that both produce insoluble phases via the foaming process.

Another important application feature for many types of foam is "stiffness," which relates to the ability of the applied foam to be stacked or piled, or for the applied foam to resist cold flow, or leveling, or exhibit a high value for its angle of repose. As a common example, for reference, lightly whipped cream will exhibit a low angle of repose and little resistance to cold flow or leveling, while good quality aerosol shaving cream can be piled easily and remain in place for hours.

When the requirement of stiffness is added to the slow drain time requirement, the list of viable foaming systems becomes quite short. The implementation of two component systems, i.e., the foaming system plus the catalyst for cross linking or curing, is particularly difficult in many industrial applications. Consequently, the useful systems are generally reduced to hydrolyzed protein foaming systems, such as those described in DiMaio U.S. Pat. No. 5,225,095 and Kittle U.S. Pat. No. 5,853,050. Each of these foaming concentrates uses ferrous ion stabilized hydrolyzed protein (from hoof and horn meal), some processing aids (lignosulfonate), and an ingredient to slow down the drain time. DiMaio uses natural gums, while Kittle uses amylopectin starch. In each of these cases, an unwanted result is that the concentrates exhibit excessive viscosity (20000 +cps). The fact that the concentrates are gels leads to other processing and application difficulties. Additionally, the stabilizing iron salts contribute to instability in the concentrate, especially when natural gums are used.

During the development of the technology described in Kittle U.S. Pat. No. 5,853,050, the utilization of common corn starch as the drain time-slowing ingredient was identified and characterized. In fact, ordinary common corn starch could have been used in the production process as the final foam product, after proper dilution, was very suitable in all respects. Unfortunately, common corn starch, generally a mixture of amylose (linear starch) and amylopectin (branched starch), exhibits a characteristic called "retrogradation," which is essentially the precipitation or coagulation of poorly soluble linear dextrins present in starch solutions. Retrogradation is described in Whistler, R. L., Bemiller, J. N., and Paschall, E. F., "Starch: Chemistry and Technology," Second Edition, Academic Press, New York, N.Y., 1984. The precipitation problem causes a second phase to form in the concentrate, thereby degrading the performance, and rendering the formulation useless. This usually occurs within a week or two, and consequently the composition is not commercially viable. The remedy for this ever present retrogradation in common corn starch was to substitute, for common corn starch, a unique starch containing essentially 100% branched material (amylopectin). This is a starch obtained from waxy maize corn and it is commonly available from major starch producers.

Making the raw material substitution allowed retrogradation to be circumvented, and thereby made the product concept commercially realistic. Negative effects associated with the stability advantage include not only the previously noted "gel-like" consistency of the final concentrate, but, in addition, an extremely high viscosity during one step of the formulation production sequence. This process nuisance required special pumping equipment as well as considerable patience on the part of the operator. Needless to say, avoiding these problems would be very much worthwhile, and, in addition, would allow preparation, in general, of higher level concentrates, which is always beneficial.

When preparing compositions using amylopectin, as in Kittle U.S. Pat. No. 5,853,050), the process scheme required the use of hot water in the initial step. As the amylopectin was added to the formulation, its viscosity increased to more than 30000 cps. In order to finish the formulation, special progressive cavity pumps were required. By the time the final ingredients had been added, the viscosity was acceptable, although still very high. This processing limitation effectively restricted the available and usable final concentration.

SUMMARY OF THE INVENTION

The foamable concentrate according to the invention comprises a cationic-modified starch, a stabilized hydrolyzed protein and water. The starch should have a degree of substitution of at least approximately 0.02, and a nitrogen content of at least approximately 0.15%. However, in a preferred foamable concentrate according to the invention, the cationic-modified starch has a degree of substitution of approximately 0.04 and a nitrogen content of approximately 0.35%.

The concentrate preferably also includes ferrous sulfate, a biocide, ammonium hydroxide, and a dispersant, preferably composed of a combination of ammonium lignosulfonate and sodium lignosulfonate.

Another aspect of the invention resides in a method of of making a foamable concentrate. The method comprises the steps of adding to water a cationic modified starch, ferrous sulfate, and a hydrolyzed protein. When the cationic modified starch is added to the water, the water should be at a temperature in the range from approximately 10° C. to 60° C., and preferably in the range from approximately 15° C. to 30° C. The cationic modified starch is preferably pre-gelatinized before it is added to the water, and preferably has a particle size distribution such that not more than about 25% by weight of the starch would pass through a 200 mesh screen.

Still another aspect of the invention resides in a method of making a stiff foam having a slow drain time. The method comprises the steps of diluting with water at ambient temperature, a foamable concentrate comprising a cationic-modified starch, a stabilized hydrolyzed protein, and water to produce a foamable liquid, and introducing a gas into the foamable liquid to produce a foam.

The invention utilizes compositions that are superior to those defined previously in DiMaio U.S. Pat. No. 5,225,095 and Kittle U.S. Pat. No. 5,853,050, in that they can be prepared using cold water and commonly available, simpler, process equipment. The process schemes do not entail excessive viscosity build-up, and the final formulations are easy to handle and process.

An additional benefit of the invention is that it allows formulation concentrates at least 50% more concentrated than those that can be achieved using either amylopectin or natural gums, while still maintaining reasonable viscosity. The benefit of greater concentration alone is valuable, as the production capacity of a process installation automatically increases because more pounds of active ingredient can be produced in every batch. The benefit of greater concentration also reduces packaging and shipping costs.

An additional benefit of the invention is simplified dilution technology. With amylopectin or natural gum compositions, the concentrate is a gel which cannot be easily diluted with water. Experience has demonstrated repeatedly that when adding these gelled materials to a dilution tank with water present the gelled compositions did not dissolve, but simply descended to the bottom of the tank, remaining essentially unaffected by the dilution water. The required remedy was to pass the dilution water in combination with the gelled concentrate through a "shearing device" in order to allow dissolution to occur. A commonly used shearing device is a gear pump, but other techniques also work well. By contrast, the modified starch formulations of the invention can disperse easily into water without excessive extra work.

A final and very important benefit of the invention is the fact that the ingredients can be varied widely to accommodate a wide array of applications. The three most important components in these formulations are: (a) the hydrolyzed protein, which makes the system capable of foaming; (2) ferrous sulfate, which can be considered, with the protein, as the "stiffening agent"; and, (3) the starch, which delivers the drain time characteristics. With high concentration compositions such as those described below, the physical characteristic, i.e., foam stiffness, can be varied independently of the chemical characteristic, i.e., drain time. The variation allowed in the dilution ratio is additionally beneficial.

DETAILED DESCRIPTION OF THE PREFERRED EMBODIMENTS

Starch Component

Figure 1:
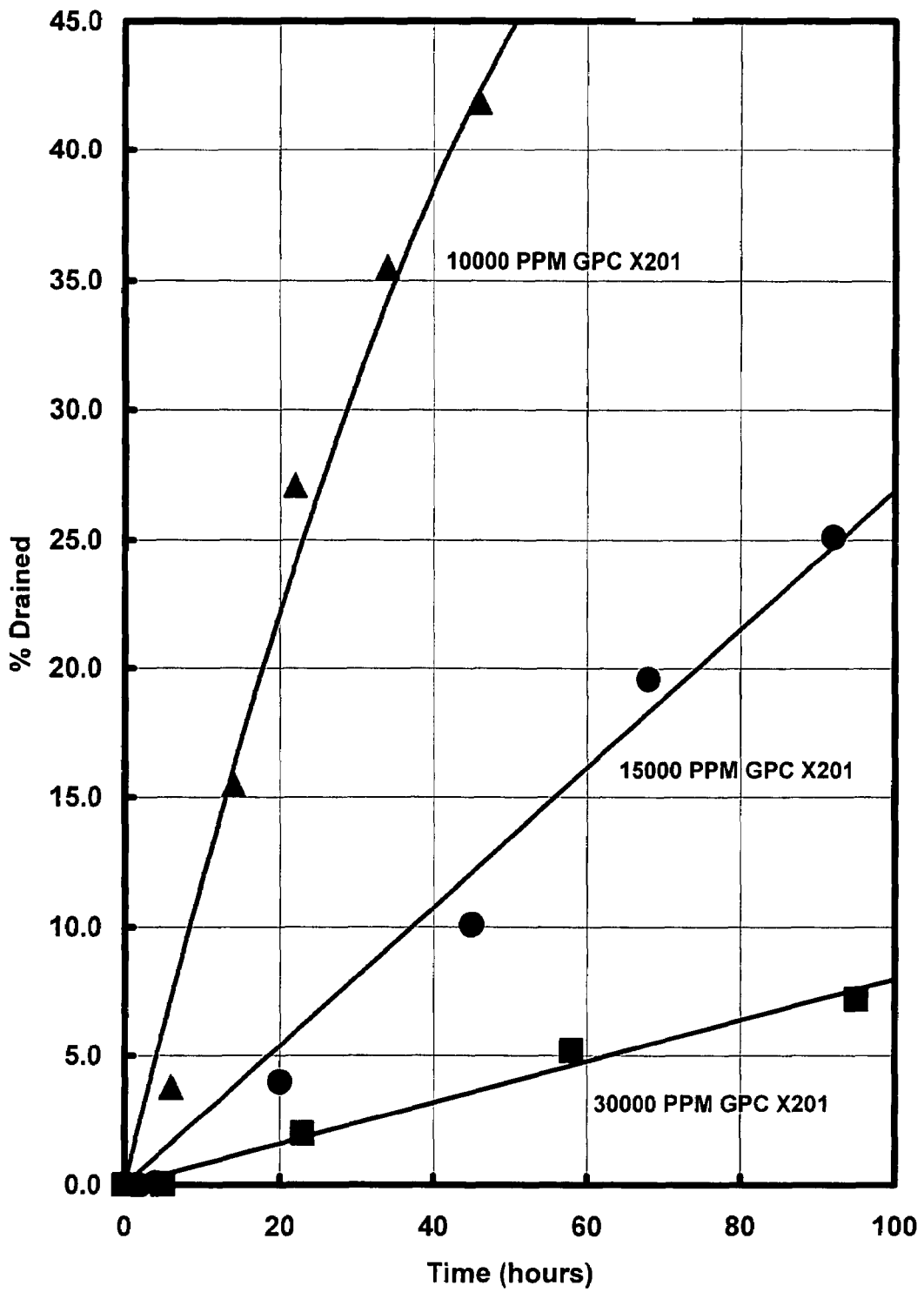
FIG. 1 is a graph comparing the drain times for foams generated using various concentrations of a first form of cationic modified starch.

As stated above, the desired characteristics of the replacement for amylopectin starch are: (1) stable dispersions exhibiting no "retrogradation"; and, (2) cold water dispersability, thereby avoiding the need for hot water. The starch industry produces starches which satisfy the stability requirement, and also produces starches which satisfy the dispersability issue, but the selection of starches satisfying both requirements is limited. An array of possible starch candidates was obtained from Cargill, National Starch, Penford Products, and Grain Processing Corporation. Only one material exhibited both of the two desired characteristics, as most of the samples were not cold water dispersible. The material that exhibited both desired characteristics was a cold water-dispersible, cationic modified starch, available from Grain Processing Corporation as an experimental product, under product number GPC X201. This material advanced to commercial status under product number GPC G400.

Cationic modified starches have been known for many years, and many examples are cited in Hofreiter, B. T., "Natural Products for Wet-End Addition," in "Pulp and Paper Chemistry and Chemical Technology," Casey, J. R., editor, Wiley, New York, N.Y., 3rd Edition, 1981, pages 1475-1514; Paschall, E. F., "Production and Uses of Cationic Starches," in "Starch Chemistry and Technology," R. L. and Paschall, E. F., editors, Academic Press, New York, N.Y., Volume II, pages 403-422; Smith, R. J., "Characterization and Analysis of Starches," also in "Starch Chemistry and Technology," Whistler, R. L. and Paschall, E. F., editors, Academic Press, New York, N.Y., Volume II, pages 569-655; and Whistler, R. L., Bemiller, J. N., and Paschall, E. F., "Starch: Chemistry and Technology," Second Edition, Academic Press, New York, N.Y., 1984.

Cationic modified starches are generally categorized by the weight percent nitrogen incorporated into the starch and the degree of substitution. The degree of substitution (DS) is a measure of the average number of hydroxyl groups on each D-glucopyranosyl unit which are derivatized by substituent groups. The DS value is expressed as moles of substituent per D-glucopyranosyl group.

The relationship between the added nitrogen content, the degree of substitution, and the molecular weight of the substituent is described by the following equation which is discussed in Whistler, R. L., Bemiller, J. N., and Paschall, E. F., "Starch: Chemistry and Technology," Second Edition, Academic Press, New York, N.Y., 1984:

$$DS=162 \times W/[100 \times M-(M-1) \times W],$$

where,

W=weight % of substituent

M=molecular weight of the substituent.

The maximum value of the degree of substitution is 3. The weight percent nitrogen is generally determined by the Dumas Method, which can be executed using a Leco Analyzer as described in "Nitrogen in Starch, Starch Slurry, and Glucose," Organic Application Note, LECO Corporation, 3000 Lakeview Avenue, St. Joseph, Mich. 49085.

The cationic modified starch used in the foamable concentrate according to the invention should have a degree of substitution of at least approximately 0.02, and in the range from approximately 0.02 to 0.2. A preferred starch for use in the invention has a degree of substitution of 0.04. The nitrogen content of the cationic modified starch should be at least approximately 0.15%, and preferably in the range from approximately 0.15% to approximately 2.0%. A preferred starch for use in the invention has a nitrogen content of 0.35%.

The Grain Processing Corporation (GPC) starch used in this development contained 0.35 weight % nitrogen, over and above the nitrogen background amount exhibited by most starches, which, as explained in Smith, R. J., "Characterization and Analysis of Starches, in "Starch Chemistry and Technology," Whistler, R. L. and Paschall, E. F., editors, Academic Press, New York, N.Y., Volume II, pages 569-655, is usually under 0.1 weight %. The corresponding degree of substitution was 0.04 moles of substituent per D-glucopyranosyl group. Hofreiter, B. T., "Natural Products for Wet-End Addition," in "Pulp and Paper Chemistry and Chemical Technology," Casey, J. R., editor, Wiley, New York, N.Y., 3$^{rd}$ Edition, 1981, pages 1475-1514 suggests that commercial cationic starches contain between 0.18 and 0.37 weight % nitrogen. According to Whistler, R. L., Bemiller, J. N., and Paschall, E. F., "Starch: Chemistry and Technology," Second Edition, Academic Press, New York, N.Y., 1984, common commercial DS values are below 0.2.

Cold water dispersability is not necessarily related to the DS value, as starch is generally a water-soluble material after the granular structure has been disrupted. This means a high DS value is not required for easy dispersion.

In many instances, with industrial starch, the gelatinizing process is performed at the user's facility, meaning that the starch producer is selling a non-gelatinized product. Granular structure disruption can be affected by pregelatinizing a starch material, and the cationic modified starch for use in the foamable concentrate of the invention is preferably pre-gelatinized, so that it can be readily combined with water. The GPC material described herein is pregelatinized, and disperses readily in cold water.

In accordance with the invention, in forming the foamable concentrate, the cationic modified starch should be added to water at a temperature in the range from approximately 10° C. to 60° C. Preferably, however, the water temperature is in the range from 15° C. to 30° C. at the time the starch is added, and ambient temperature, i.e., approximately 20° C. to 25° C., is entirely suitable.

It is important to note that the foam technology benefits achieved by this development are related to the starch stability provided by the cationic substituents, while the process benefits are related to the pregelatinizing of the starch raw material. As mentioned above, the starch industry does offer an array of cationic starches. Thus foam technology benefits could be obtained by cooking these non-dispersible cationic starches, thereby gelatinizing them on-site. Another alternative is to purchase from the starch supplier a predispersed cationic starch, which, by definition, would have been gelatinized. These are all process alternatives and each leads to essentially the same foam technology benefits.

Raw Material Sources

In the following examples, the hydrolyzed keratin protein was produced by Industria Suma Ltda in Brazil, and can be obtained from Martin Baer & Co. P. O. Box 11, Essex, Conn. 06426, U.S.A. The amylopectin starch can be obtained from Cargill, Inc., P. O. Box 9300, Minneapolis, Minn., 55440, U.S.A., or National Starch and Chemical Company, 10 Finderne Avenue, Bridgewater, N.J. 08807, U.S.A. The ferrous sulfate is commonly available and is preferred as the heptahydrate, $FeSO_4 \cdot 7H_2O$. The TSFL dispersant, a combination of ammonium and sodium lignosulfonate, is available from Lignotech USA Inc., 100 Grand Avenue, Rothchild, Wis. 54474, U.S.A. The biocide can be Stepan Onyxide, from Stepan Company, 22 W. Frontage Road, Northfield, Ill., 60093, U.S.A., or Nipacide BK, from Nipa Hardwicke, Inc., 3411 Silverside Road, 103 Hagley Building, Wilmington, Del. 19810, U.S.A., or an equivalent biocide. Ammonium hydroxide is used to adjust the pH to about 6.5. The cationic starch is commercially available from Grain Processing Corporation, 1600 Oregon Street, Muscatine, Iowa 52761.

Formulation Procedures

In making a foamable concentrate using the GPC starch compositions, the required amount of ambient temperature water was placed in a reactor vessel equipped with a stirrer suitable for the batch size. The dry and liquid ingredients were added while stirring was maintained. No heat was added. Modest viscosity was exhibited, but only at the higher solids levels. The components were added in the following order: GPC G400 cationic modified starch, ferrous sulfate heptahydrate, hydrolyzed protein, TSFL dispersant, ammonium hydroxide, and finally the biocide. Stirring was continued for a time interval sufficient to achieve a homogeneous final mixture, generally between three and ten hours, depending on batch size.

In addition, the particle size of the cationic modified starch is important from a process viewpoint, but that variable does not affect the foam properties of importance, namely stiffness and drain time. In some of the development work described herein, GPC X201, a developmental cationic modified starch having a larger particle size, was used. Only about 25% of the material, by weight, would pass through a 200 mesh screen.

GPC G400, a commercial cationic modified starch, having a smaller particle size, was also used in the development work. In the case of GPC G400, more than 60% of the material would pass through a 200 mesh screen.

The commercial material having a smaller particle size was more difficult to disperse in that, like many wettable powders, the material formed small globules of dry material which required extra stirring time in the reactor before complete dispersion was achieved. The larger particle size material is preferred not only because it dispersed much more easily, but also because it resulted in less dust and was therefore more comfortable to use.

The process schemes provided an opportunity to introduce many variables in the hope that the formulation produced would be better, or that the process itself would be faster or more efficient. A common first choice is to alter the temperature of the formulation process, anticipating that the dispersion sequence will accelerate. In fact, no significant dispersion speed advantage was realized. However, at a higher temperature, the viscosity of the final formulation is very much higher. The same result occurs if a formulation produced at room temperature is subjected to heating after the normal room temperature process is completed. In all cases, heating generates a more viscous concentrate.

Foaming Performance

After a particular composition was prepared and its physical properties defined, the only other laboratory evaluation available was performed. This evaluation involved foaming the diluted material, judging the physical characteristics of the foam produced, and measuring the drain time.

Dilution

Since the compositions are essentially all the same, and vary only with respect to concentration, the diluted, "to-be-foamed" liquid of a specific composition can be obtained from any of the compositions. Common practice involves diluting according to the "dilution ratio," which is defined as the volume of the diluted material divided by the volume of the concentrate. As an example, when one volume of concentrate is added to six volumes of water, the total volume is seven units, and the dilution ratio is seven. In the following examples, the dilution was adjusted to prepare "to-be-foamed" liquids with specific levels of GPC G400 starch, since that ingredient is directly related to the drain time performance.

Foaming Equipment

The foaming procedure is described in Kittle U.S. Pat. Nos. 4,874,641, 5,215,786, 5,853,050, 6,929,423, and 6,994,491, and is based on technology originally described in Kroll U.S. Pat. No. 4,474,680. The disclosures of all of these patents are here incorporated by reference. The "to-be-foamed" liquid is pumped through a flow control orifice into a mixing block, where it is added to an expansion gas, usually compressed air, similarly controlled by a flow control orifice. The combination is discharged through a mixing zone, which can be constituted by a hose of appropriate length or by a packed bed, so that a foam is discharged onto a target substrate. The technology is fully scalable, with commercial devices having a discharge rate ranging from less than one gallon per minute liquid flow to 60 gallons per minute liquid flow.

Drain Time Measurement

Measuring the drain time for these compositions entails measurement of the "relative" drain time rather than attempting to define and measure absolute drain time, which is much more complex. In these cases, all that is required is a standard procedure which is: (a) reproducible; (b) easy to carry out; and (c) related to common field experience. A drain time procedure satisfying these requirements has been developed and calibrated. The procedure involves the use of a foaming system, as described above, operating at one gallon per minute liquid flow, which becomes the definition of how much liquid is collected as foam. This discharge is collected for one minute in a fifteen gallon plastic tank having a conical bottom and fitted with a gravity discharge opening at the bottom of the cone. After the calibrated foaming system has stabilized, the foam is discharged into the plastic tank for one minute.

The beginning of the time interval (t=0) used as the measure of drain time is determined to be the time of completion of the discharge of foam into the tank. A collection beaker is set below the bottom of the tank. As the foam drains, liquid is collected, and the weight is incrementally defined as a function of time. Since the input volume was one gallon, that is, 3785 cubic centimeters, the grams collected in each time interval can be converted to weight percent drained by dividing by 37.85. The final result can be plotted as weight percent drained as a function of time. The procedure is reliable, and works best for foams having slower drain times.

In the following examples, viscosity was measured after the material was allowed to rest overnight. The viscosity measurements were made using a Brookfield viscometer, at spindle #4 speeds of 6, 12, 30 and 60 rpm.

EXAMPLES OF COMPOSITIONS

Example One

For reference, a typical commercial batch of product, in accordance with Kittle U.S. Pat. No. 5,853,050, prepared by the procedure previously outlined had the following composition:

| Keratin protein | 4.00 | weight percent |
|---|---|---|
| Amylopectin starch | 4.00 | |
| Ferrous sulfate | 8.00 | |
| TSFL | 4.00 | |
| Biocide | 0.50 | |
| Ammonium hydroxide | 0.40 | |
| Water | 79.10 | |
| Total | 100.00 | |

The physical characteristics of this composition are: (a) pH at room temperature, 6.2-6.4; (b) weight percent solids, 15.50; (c) viscosity after the material was allowed to rest overnight, measured using a Brookfield viscometer, at room temperature, at spindle #4 speeds of 6, 12, 30, 60, was 19000, 10000, 4800, 3000 cps, respectively.

Example Two

By contrast when the same composition is prepared using the same ingredients, but omitting the amylopectin and substituting Grain Processing Corporation's X201 cationic modified starch, the composition was as follows:

| Keratin protein | 4.00 | weight percent |
|---|---|---|
| GPC X201 starch | 4.00 | |
| Ferrous sulfate | 8.00 | |
| TSFL | 4.00 | |
| Biocide | 0.50 | |
| Ammonium hydroxide | 0.40 | |
| Water | 79.10 | |
| Total | 100.00, | | the physical characteristics were identical to those of Example One, except that the viscosity was less than 100 cps.

Example Three

In this example, the composition of Example Two was extended to a higher starch level, and was as follows:

| Keratin protein | 4.00 | weight percent |
|---|---|---|
| GPC X201 starch | 6.00 | |
| Ferrous sulfate | 8.00 | |
| TSFL | 4.00 | |
| Biocide | 1.00 | |
| Ammonium hydroxide | 0.50 | |
| Water | 76.50 | |
| Total | 100.00, | |

The increased starch content did not significantly increase the viscosity. The pH remained in the same range, and the solids increased to 17.49. Repetition of the same composition demonstrated the expected reproducibility.

Example Four

In order to evaluate how far the concentration level could be extended, the components of the formulation (other than the biocide) were proportionately increased, by 25%, while the amount of water was correspondingly decreased, so that the formulation was as follows:

| Keratin protein | 5.00 | weight percent |
|---|---|---|
| GPC X201 starch | 7.50 | |
| Ferrous sulfate | 10.00 | |
| TSFL | 5.00 | |
| Biocide | 1.00 | |
| Ammonium hydroxide | 0.60 | |
| Water | 70.90 | |
| Total | 100.00 | |

The solids increased to 21.12%, the pH remained at 6.3, and the viscosity showed some increase. The viscosity at room temperature, measured using a Brookfield viscometer, with spindle #4 speeds of 6, 12, 30, 60, resulted in measured viscosities of 2000, 1500, 1200, and 1100 cps, respectively, all of which are well within a usable viscosity range.

Example Five

In this example, the composition was again proportionately increased by about 25% to arrive at the following composition:

| Keratin protein | 6.00 | weight percent |
|---|---|---|
| GPC X201 starch | 9.00 | |
| Ferrous sulfate | 12.00 | |
| TSFL | 6.00 | |
| Biocide | 1.00 | |
| Ammonium hydroxide | 0.70 | |
| Water | 65.30 | |
| Total | 100.00 | |

The solids increased to 25.31%, the pH stayed the same at 6.3, while the viscosity increased. The viscosity at room temperature, measured using a Brookfield viscometer, with spindle #4 speeds of 6, 12, 30, 60, resulted in measured viscosities of 9000, 6000, 3800, and 2700 cps, respectively, all of which are still within a usable viscosity range, even though some gel formation was observed.

Example Six

The following formulation was prepared at room temperature, yielding a concentrate having a pH of 6.5, and spindle #4 viscosities of 2180, 1470, 945, and 510 cps, with spindle speeds of 6, 12, 30, and 60, respectively. The measurements were taken at 25° C. This composition used GPC G400 cationic modified starch, the commercial version of the GPC X201 starch described previously.

| Keratin protein | 4.00 | weight percent |
|---|---|---|
| GPC G400 starch | 9.00 | |
| Ferrous sulfate | 8.00 | |
| TSFL | 4.00 | |
| Biocide | 1.00 | |
| Ammonium hydroxide | 0.60 | |
| Cinnamon Scent | 0.10 | |
| Water | 73.30 | |
| Total | 100.00 | |

Example Seven

A formulation corresponding to that of Example Six was prepared, but at a temperature of 50-55° C. The corresponding viscosities were 6300, 4200, 2820, 2020 cps, also at 25° C.

Example Eight

A sample of a scaled-up batch of the Example Six composition was reheated to 60-65° C. for three hours while being stirred modestly. After cooling and sitting at rest overnight, the same procedures as used for all the samples, the viscosities were measured at 25° C., with spindle #4 and the same rotational speeds, yielding viscosity values of 40000, 25900, 15200, and 9900 cps.

The foaming performance and drain time results for samples according to Examples Six, Seven and Eight, all evaluated under the same conditions, were essentially identical. An explanation for this behavior is that the fluid characteristics of the various concentrates are a function of the processing history, but, when each concentrate is diluted to the same "to-be-foamed" composition, the fluid characteristics become identical.

Example Nine

The following composition, which is identical to the composition of Example Three, was prepared at room temperature, yielding expected physical properties:

| | | |
|---|---|---|
| Keratin protein | 4.00 | weight percent |
| GPC X201 starch | 6.00 | |
| Ferrous sulfate | 8.00 | |
| TSFL | 4.00 | |
| Biocide | 1.00 | |
| Ammonium hydroxide | 0.50 | |
| Water | 76.50 | |
| Total | 100.00 | |

The composition was diluted at a dilution ratio of 6, by adding 7.5 pounds of the composition to 37.5 pounds of cold water. The mixture was stirred for a few minutes and foamed directly, as described above. The GPC X201 composition in the diluted "to-be-foamed" liquid was 10000 ppm, which was the original composition, 60000 ppm, divided by the dilution ratio. The foam produced was stiff by any common standard and the drain time was measured as described. The drain time results are shown in FIG. 1.

When the same composition was diluted at a dilution ratio of 4, by adding 10.0 pounds of the composition to 30 pounds of cold water, the resulting foam was stiffer. The amount of GPC X201 starch in the diluted, "to-be-foamed," liquid was 15000 ppm, which was the original composition, 60000 ppm, divided by the dilution ratio. The drain time results are also shown in FIG. 1.

When the same composition was diluted at a dilution ratio of 2, by adding 8000 grams of the composition to 8000 grams of cold water, the resulting foam was extremely stiff. The GPC X201 composition in the diluted, "to-be-foamed," liquid was 30000 ppm, which was the original composition, 60000 ppm, divided by the dilution ratio. The drain time results are shown in FIG. 1.

Evaluation of the effect of the starch concentration on the drain time results shows a generally proportional relationship between starch content and drainage. As an example, at 20 hours, the 10000 ppm composition drained about 22% while the 30000 ppm composition drained about 2%. When making the same comparison at 40 hours, the values are 38% and 3%, respectively. Within this range of concentrations, tripling the starch level, 10000 ppm to 30000 ppm, produced a ten fold decrease in the percentage of the foam, which is exactly the effect being sought.

Example Ten

A generally acceptable formulation can be prepared using the following composition, which is the same as the composition of Example Six, but made in a larger batch size.

| | | |
|---|---|---|
| Keratin protein | 4.00 | weight percent |
| GPC G400 starch | 9.00 | |
| Ferrous sulfate | 8.00 | |
| TSFL | 4.00 | |
| Biocide | 1.00 | |
| Ammonium hydroxide | 0.60 | |
| Cinnamon Scent | 0.10 | |
| Water | 73.30 | |
| Total | 100.00 | |

The cinnamon is added to mask the hydrolyzed protein odor some find objectionable. The solids for this composition are 20.16% and the pH at 20° C. is 6.4. The viscosity profile, after overnight at rest, also at 20° C., was 4100, 2800, 1960, and 1420 cps at spindle #4 speeds of 6, 12, 30, 60 rpm, respectively.

Figure 2:
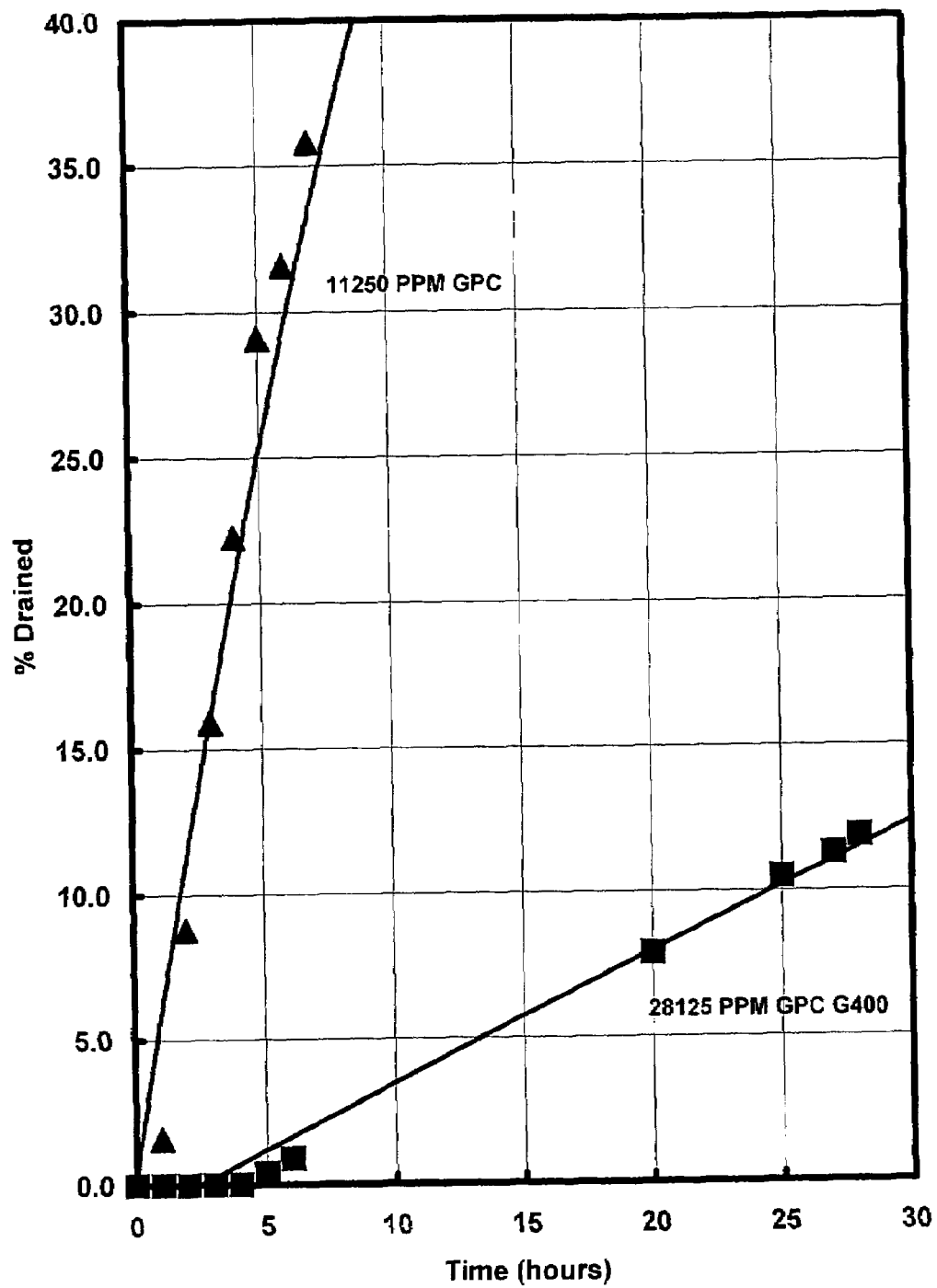
FIG. 2 is a graph comparing the drain times for foams generated using two concentrations of a second form of cationic modified starch having a smaller particle size than that of the first form of cationic modified starch.

The development work demonstrated that this formulation achieved a suitable balance between the physical properties of the concentrate and foam performance at various dilution ratios, while various application issues were being considered. The drain time measurements were made at dilution ratios of 8.0 (G400 at 11250 ppm) and 3.2 (G400 at 28125 ppm). The drain time results are shown in FIG. 2.

Example Eleven

Alternatively, a generally acceptable formulation can be prepared using the following composition, which is the same as the composition of Example Ten, but made using the cationic starch in slurry form.

| | | |
|---|---|---|
| Keratin Protein | 4.00 | weight percent |
| GPC L435 Starch (30%) Slurry | 30.00 | |
| Ferrous sulfate heptahydrate | 8.00 | |
| TSFL | 4.00 | |
| Biocide | 1.00 | |
| Ammonium hydroxide | 0.60 | |
| Cinnamon Scent | 0.10 | |
| Water | 52.30 | |

The cinnamon is added to mask the hydrolyzed protein odor. The solids for this composition are 20.1% and the pH at 26° C. is 6.4. The viscosity profile, after overnight at rest, at 25° C., was 360, 200, 190, 175 cps at spindle #2 speeds of 6, 12, 30 and 60 rpm, respectively. Subsequent development work demonstrated that this formulation achieved a suitable balance between the physical properties of the concentrate and foam performance at various dilution ratios, while various application issues were being considered. The drain time measurements were made at a dilution ratio of 8.0 (L435 at 11250 ppm). The drain time results are essentially the same as those depicted in FIG. 2 for G400 at 11250 ppm.

APPLICATIONS

The formulations as herein described offer a broad array of foam product performance factors unavailable from any other compositions. The basic components in a concentrate formulation can allow foaming with both stiffness and drain time control initially defined by the weight percent levels of the ingredients. Since the compositions can be prepared at relatively high weight percent levels, the dilution ratio used in the field now can offer an increased range of performance.

There are many applications for the invention. In landfill and hazardous waste applications, discussed by many of the patent references, stiffness and persistence are key performance factors. Some mining applications utilize very stiff foams for controlling low pressure differential air flows. In these cases, extreme stiffness may be needed to avoid cold flow or self-leveling.

Forced recovery of landfill gas (methane) as described by Kittle in U.S. Pat. No. 6,929,423, requires good drain time control, but not necessarily excessive stiffness, since the foam is injected into a horizontal distribution pattern, and the foam should not drain significantly until such time as the application is completed.

On the other side of the spectrum, the iron component of the protein complex can be useful for controlling hydrogen sulfide as described by Kittle in U.S. Pat. No. 6,994,491, where the foam also needs to be injected into reasonably compacted material. This attribute can also be extended to the control of hydrogen sulfide during mining operations, provided that the contact between the foam phase and the escaping gas is efficient. In coal mining operations, this requires foam application at the cutting interface, thereby minimizing the time between contact and control, compared to the time required for the gas to escape into the environment. In mining, the same technology can also control dust generated by the cutting operation.

What is claimed is:

1. A method of making a foamable concentrate comprising the steps of adding to water a pre-gelatinized cationic modified starch having a degree of substitution of at least approximately 0.02 and a nitrogen content of at least approximately 0.15%, and a stabilized hydrolyzed protein.

2. The method according to claim 1, in which, when the pre-gelatinized cationic modified starch is added to the water, the water is at a temperature in the range from approximately 10° C. to 60° C.

3. The method according to claim 1, in which, when the pre-gelatinized cationic modified starch is added to the water, the water is at a temperature in the range from approximately 15° C. to 30° C.

4. The method according to claim 1, in which the pre-gelatinized cationic modified starch, when added to the water, has a particle size distribution such that not more than about 25% by weight of the starch would pass through a 200 mesh screen.

5. A method of making a stiff foam having a slow drain time comprising the steps of:
   making a foamable concentrate by adding to water a pre-gelatinized cationic modified starch having a degree of substitution of at least approximately 0.02 and a nitrogen content of at least approximately 0.15%, and a stabilized hydrolyzed protein;
   diluting said foamable concentrate with water to produce a foamable liquid; and
   introducing a gas into the foamable liquid to produce a foam.

6. The method according to claim 5, in which, when the pre-gelatinized cationic modified starch is added to the water, the water is at a temperature in the range from approximately 10° C. to 60° C.

7. The method according to claim 5, in which, when the pre-gelatinized cationic modified starch is added to the water, the water is at a temperature in the range from approximately 15° C. to 30° C.

8. The method according to claim 5, in which the pre-gelatinized cationic modified starch, when added to the water, has a particle size distribution such that not more than about 25% by weight of the starch would pass through a 200 mesh screen.

9. The method according to claim 5, in which, when said foamable concentrate is diluted with water, the water with which said foamable concentrate is diluted is at ambient temperature.

10. The method according to claim 5, in which the pre-gelatinized cationic-modified starch has a degree of substitution in the range from approximately 0.02 to 0.2.

11. The method according to claim 5, in which the pre-gelatinized cationic-modified starch has a nitrogen content in the range from approximately 0.15% to 2.0%.

12. The method according to claim 5, in which the pre-gelatinized cationic-modified starch has a degree of substitution in the range from approximately 0.02 to 0.2 and a nitrogen content in the range from approximately 0.15% to 2.0%.

13. The method according to claim 5, in which the pre-gelatinized cationic-modified starch has a degree of substitution of approximately 0.04.

14. The method according to claim 5, in which the pre-gelatinized cationic-modified starch has a nitrogen content of approximately 0.35%.

15. The method according to claim 5, in which the pre-gelatinized cationic-modified starch has a degree of substitution of approximately 0.04 and a nitrogen content of approximately 0.35%.

16. The method according to claim 5, in which the foamable concentrate, when diluted with water in the dilution step, also comprises ferrous sulfate.

17. The method according to claim 5, in which the foamable concentrate, when diluted with water in the dilution step, also comprises a dispersant.

18. The method according to claim 5, in which the foamable concentrate, when diluted with water in the dilution step, also comprises a dispersant composed of a combination of ammonium lignosulfonate and sodium lignosulfonate.

19. The method according to claim 5, in which the foamable concentrate, when diluted with water in the dilution step, also comprises ammonium hydroxide.

20. The method according to claim 5, in which the foamable concentrate, when diluted with water in the dilution step, also comprises ferrous sulfate, a biocide, ammonium hydroxide, ammonium lignosulfonate and sodium lignosulfonate.

* * * * *